United States Patent [19]

Svenson et al.

[11] Patent Number: 5,409,008
[45] Date of Patent: Apr. 25, 1995

[54] PROCESS AND APPARATUS FOR MAPPING OF TACHYARRHYTHMIA

[75] Inventors: Robert H. Svenson, Charlotte, N.C.; Gregory G. Brucker, Minneapolis; Steven D. Savage, Brooklyn Center, both of Minn.

[73] Assignee: Angeion Corporation, Minneapolis, Minn.

[21] Appl. No.: 83,200

[22] Filed: Jun. 25, 1993

Related U.S. Application Data

[63] Continuation of Ser. No. 647,986, Jan. 30, 1991, abandoned.

[51] Int. Cl.$^6$ .................. A61B 5/04; A61N 1/04
[52] U.S. Cl. .................. 128/642; 607/119; 607/122
[58] Field of Search .......... 128/642, 658, 705, 639; 606/32, 41, 45, 46, 48, 49, 50, 2, 15, 41; 607/115, 122, 119

[56] References Cited

U.S. PATENT DOCUMENTS

| | | | |
|---|---|---|---|
| 4,519,389 | 5/1985 | Gudkin et al. | 606/20 |
| 4,660,571 | 4/1987 | Hess et al. | 606/15 |
| 4,784,133 | 11/1988 | Mackin . | |
| 4,785,815 | 11/1988 | Cohen . | |
| 4,832,048 | 5/1989 | Cohen | 128/642 X |
| 4,928,695 | 5/1990 | Goldman et al. | 128/786 X |
| 4,940,064 | 7/1990 | Desai | 128/786 X |
| 4,985,028 | 1/1991 | Isner et al. | 606/15 |
| 5,019,075 | 5/1991 | Spears et al. | 606/15 |
| 5,056,517 | 10/1991 | Fenici | 128/786 X |
| 5,083,565 | 1/1992 | Parins | 606/41 |
| 5,104,393 | 4/1992 | Isner et al. | 606/15 |
| 5,111,832 | 5/1992 | Saksena | 606/2 |
| 5,140,987 | 8/1992 | Schger et al. | 606/15 |

FOREIGN PATENT DOCUMENTS

WO8704081  7/1987  WIPO .

Primary Examiner—Lee S. Cohen
Assistant Examiner—Samuel Gilbert
Attorney, Agent, or Firm—Patterson & Keough

[57] ABSTRACT

Process and apparatus for mapping of tachyarrhythmia, such as ventricular tachycardia. The apparatus is a mapping catheter which is a polymer member including a plurality of electrodes at a distal end. An upper ring is divided into at least bipolar poles for sensing endocardial potentials. A spaced lower unipolar ring senses intercardic potentials. The process provides for sensing of a QRS signal with the upper bipolar electrodes, and the unipolar ring provides for sensing of the EKG signal. The mapping catheter is of such a size that the mapping catheter can be inserted up and through a hand-held probe to steer and guide the mapping catheter. An interventional catheter will fit within the mapping catheter for ablation of arrhythmogenic sites. One embodiment is a laser delivery catheter which can include a fiber optic cable, a fixation wire, a metal sensing tip and an internal flushing lumen.

9 Claims, 4 Drawing Sheets

PROCESS AND APPARATUS FOR MAPPING OF TACHYARRHYTHMIA

CROSS REFERENCES TO CO-PENDING APPLICATIONS

This is a continuation of application Ser. No. 07/647,986, filed Jan. 30, 1991, now abandoned.

BACKGROUND OF THE INVENTION

Definitions

A. VT—Ventricular tachycardia.

B. Active Site—Critical site to deliver ablation energy to cure VT or tachyarrhythmia in general identified by electrical activations. The energy must be delivered to the heart tissue to ablate the heart tissue.

C. Diastolic—That period of time between two QRS complexes of the electrocardiogram.

D. Ablation—The delivery of destructive energy to the cardiac tissues containing the active site, which alters the electrophysiological character of the tissue, but does not vaporize the tissue itself.

FIELD OF THE INVENTION

The present invention pertains to systems for treatment of any tachycardia, including ventricular tachycardia, and more particularly, pertains to a mapping catheter for mapping of ventricular tachycardia, as well as the process of using the same. The present invention is also referred to as a "catheter".

DESCRIPTION OF THE PRIOR ACT

Prior art mapping catheters have not provided for the mapping of QRS signals, as well as electrocardiogram (EKG) signals at the same time, and particularly mapping of active origins of ventricular tachycardia.

In existing technology, the recognition of the site of the origin of the arrhythmias and the ablation function are performed separately. For ventricular tachycardia, there has been no consensus of opinion as to what electrical activation time constitutes the "site of origin". Furthermore, the ablation energy source, whether DC current shock, radio frequency, or laser, has to be separately redirected by visual means to the site of suspected origin of the arrhythmia. Arrhythmia ablation is currently performed during open heart surgery or through catheters directed percutaneously through the heart. During the surgical approach, either a hand-held electrical mapping probe or a computerized array of electrodes acquire electrical activation data seeking the site of origin of the arrhythmia. In the percutaneous catheter based approach, a catheter with recording electrodes is positioned in the heart under fluoroscopic guidance.

Following acquisition of electrical activation data, ablation energy is then later delivered by hand-held probes or catheters either in the operating room or in the cardiac catheterization lab.

In the prior art, the process for identification of the "site of origin" of the arrhythmia was performed with electrical recording procedures designed to map the spread of electrical activation in the heart looking for the site of earliest electrical activation (site of origin). This procedure is carried out by sequentially moving a hand-held electrical recording probe or catheter over the heart and recording the time of arrival of the electrical impulse to that location. This process turned out to be a long and tedious procedure.

Prior art mapping procedures also include a sock multiple electrode array (epicardial), a balloon endocardial electrode array, a single hand-held mapping probe or a multiple electrode catheter (endocardial) inside a chamber of the heart. These procedures require a skilled surgeon and cardiac electrophysiologist.

The prior art mapping procedures are capable of reconstructing the spread of electrical activation in the heart, but do not in themselves identify the "active site" of the arrhythmia, can be time consuming, and are separate functions from the prior art ablation procedures.

The present invention overcomes the disadvantages of the prior art by providing a new and novel mapping catheter, particularly a mapping catheter which can also be used as an ablation catheter or in combination with ablation catheters passed through a hollow lumen. In addition, the mapping catheter can also be used to irradicate the site of a tachyarrhythmia including ventricular tachycardia using DC or RF energy, or in the alternative, using a laser delivery catheter for irradiation of the endocardial surface.

SUMMARY OF THE INVENTION

The general purpose of the present invention is to provide a mapping catheter for mapping of active origins of ventricular tachycardia, and in general, any tachyarrhythmia including ventricular tachycardia.

According to one embodiment of the present invention, there is provided a mapping catheter which includes a polymer member, bipolar sensing electrodes placed on a distal end of said polymer member, a spaced unipolar electrode at a spaced distance from said bipolar electrodes, and a lumen within said polymer member for the passage of a laser catheter or other instrument.

This catheter reduces to practice a medical procedure which can be an alternative to current interoperative treatment modalities for ventricular tachycardia, such as surgical resection, cryroblation, and laser irradiation. These procedures generally have a mortality rate of 10 to 20%, which is a direct result of ventriculotomy done to expose the inside surface of the left ventricle. The current catheter allows for a treatment modality which obviates the need for the ventriculotomy, thus reducing patient mortality and morbidity. An additional benefit of such a procedure is that a more normal physiological environment, i.e. heart beating, blood flow, body temperature and myocardial tissue intact, will allow for identification and elimination of ventricular tachycardia sites more reliably and accurately. Lastly, such a procedure could either be used as an adjunct to or instead of an implantable defibrillators (AICD), thus possibly eliminating the substantial lifestyle changes required of patients with AICDS.

The current catheter provides a tool for more accurately mapping the electric potential of very small areas of the inner chambers of the heart. In addition, the catheter provides a way to simultaneously obtain the QRS and EKG signals, thus providing a method to more rapidly and accurately identify the focus or foci of the tachycardia. One such method of identifying such sites is disclosed in patent applications by Svenson, et al., U.S. Ser. No. 07/601,249, filed Oct. 19, 1990, entitled "Process of Identification of a Ventricular Tachycardia (VT) Active Site and an Ablation Catheter System"; and Svenson et al., U.S. Ser. No. 07/601,241, filed Oct. 19, 1990, entitled "Process of Identification of an active Site of Ventricular Tachycardia and for Electrode Attachment of an Endocardial Defibrilator".

In addition to identifying the sites, the poles of the mapping catheter can be used to ablate the focus of the tachycardia by using radio frequency or DC current energy processes. Additionally, a laser delivery catheter can be passed through the center hollow lumen of the mapping catheter and the myocardium irradiated for a predetermined period of time to ablate the site.

One significant aspect and feature of the present invention is a mapping probe which is procedurally effective in mapping, as well as ablation of active origins.

Another significant aspect and feature of the present invention is a mapping catheter with a plurality of electrodes with a hollow lumen for passage of an instrument such as a laser catheter or any other operative instrument.

Having thus described the preferred embodiments of the present invention, it is a principal object hereof to provide a process and apparatus for mapping of tachyarrhythmia, such as ventricular tachycardia, and particularly, a mapping catheter. The mapping catheter is hand-held, requires a hole in the heart of minimal diameter for insertion, such as in the left ventricle, and maps a QRS signal, as well as an EKG signal.

One object of the present invention is to provide a mapping catheter which can also accommodate a catheter for ablation of an active origin, or itself be used to ablate the active sites with passage of energy through the electrodes.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
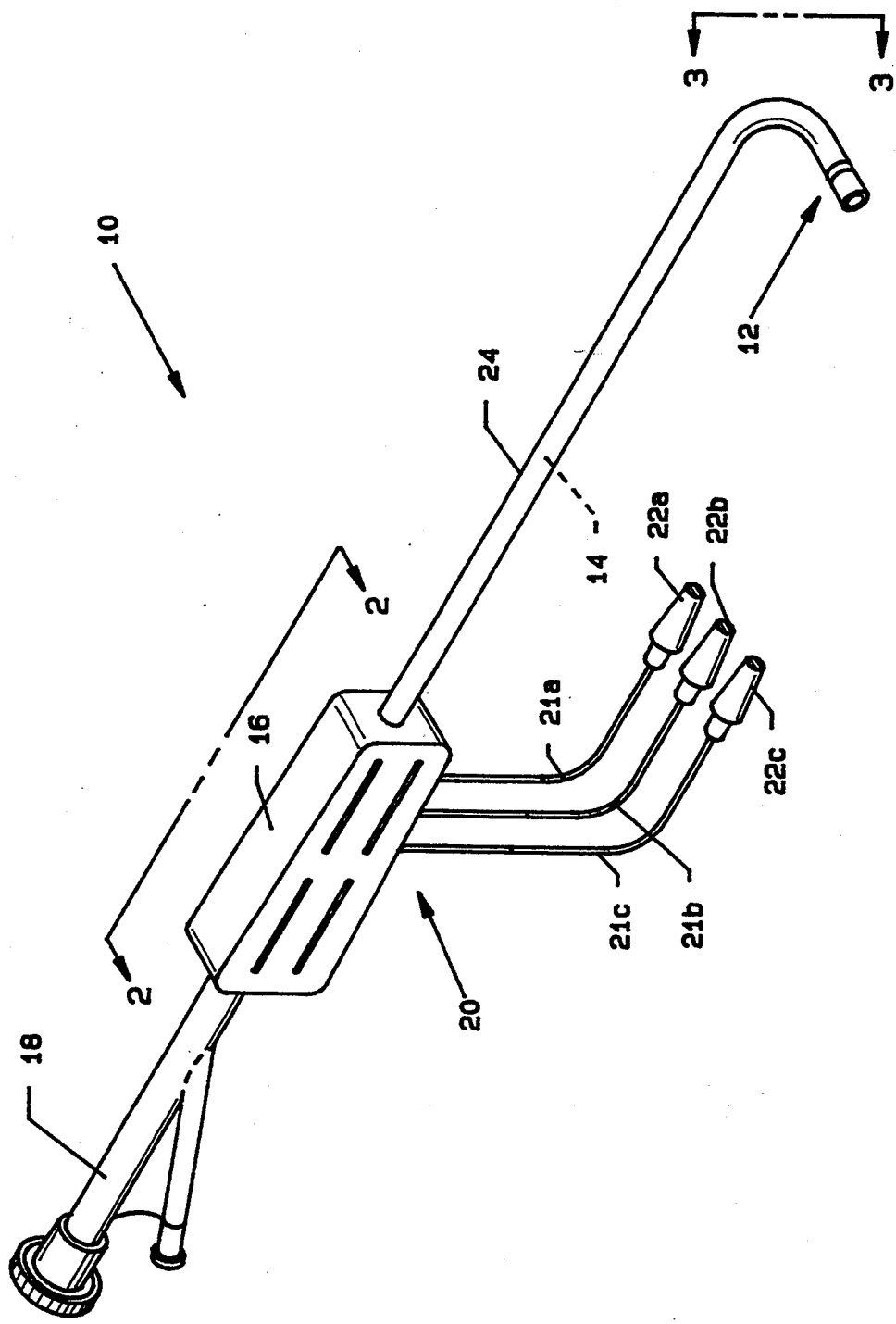
FIG. 1 illustrates a perspective view of the mapping catheter.

FIG. 1 illustrates a perspective view of the mapping catheter 10 including the catheter tip 12, the stainless steel support tube 14, the hand piece 16, and the Y-connector 18. The hand piece 16 joins the Y-connector 18 and the stainless steel support tube 14 together and includes the electrical junction 20 of the wires 21a–21c with electrical connectors 22a–22c, which in this example are insulated alligator clips. A polymer tube-like sheath 24 connects between the catheter tip 12 and the hand piece 16, and houses a plurality of wires 21a–21c between the polymer sheath 24 and the underlying stainless steel support tube 14.

Figure 2:
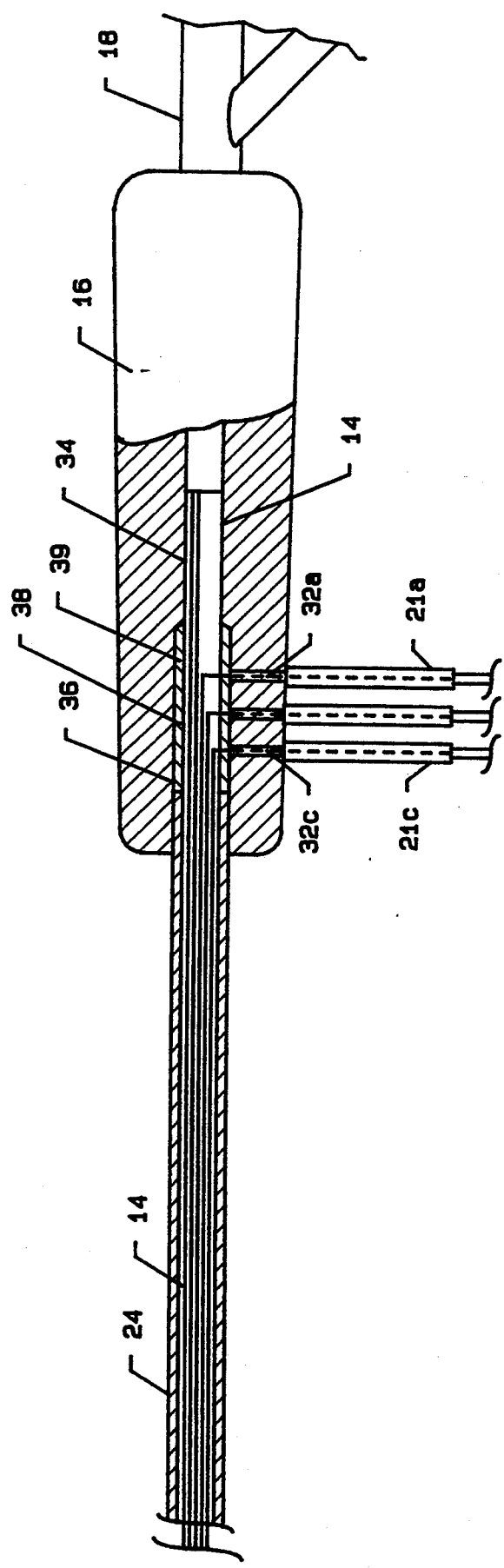
FIG. 2 illustrates a partial cross section of the hand piece.

FIG. 2 illustrates a view of the hand piece 16 in partial cross section including the stainless steel support tube 14, a flexible polymer sheath 24, shown in cross section, for the capturing of the wires 21a–21c, and the Y-connector 18 at the other end. Polymer sheath 24 frictionally engages longitudinal lumen 34. The wires 21a–21c pass through holes 32a–32c in the hand piece 16 and align along the route surface of the stainless steel support tube 14. The wires 21a–21c travel through the holes 32a–32c, through the cavity area 38 of a larger hole 36, and then along the surface of the stainless steel support tube 14. The cavity area 38 is then filled with a polymer 39 to seal the wires 21a–21c and also to additionally secure the stainless steel support tube 14 to the hand piece 16. The polymer sheath 24 aligns over and about the wires 21a–21c and the stainless steel catheter support tube 14 to provide for support of the wires.

Figure 3:
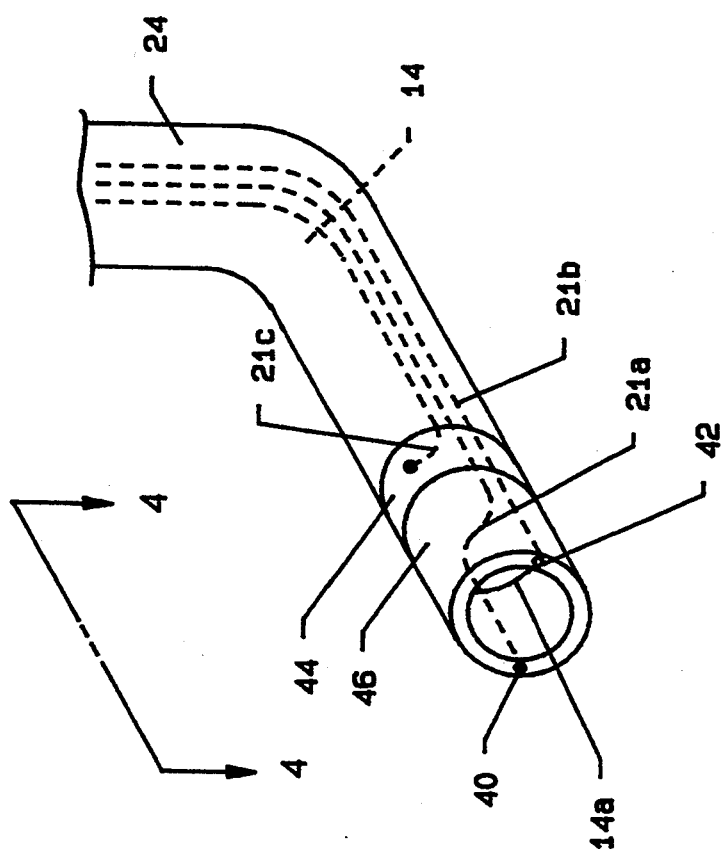
FIG. 3 illustrates an enlarged view of the electrode tip.

FIG. 3 illustrates an enlarged perspective view of the catheter tip 12 of the mapping catheter 10 including the bipolar electrodes 40 and 42, and the unipolar electrode 44 about the polymer member 46. The polymer member 46 extends about the tip 14a of the stainless steel support tube 14. The tubular polymer member 46 is described in detail in FIG. 4. Wires 21a–21c connect from the electrodes 42, 44 and 46 are contained in the polymer sheath 24, and travel through the electrical junction 20 to the electrical connectors 22a–22c illustrated in FIG. 1. The electrodes can assume any geometrical configuration and can be made of any suitable conductive material.

Figure 4:
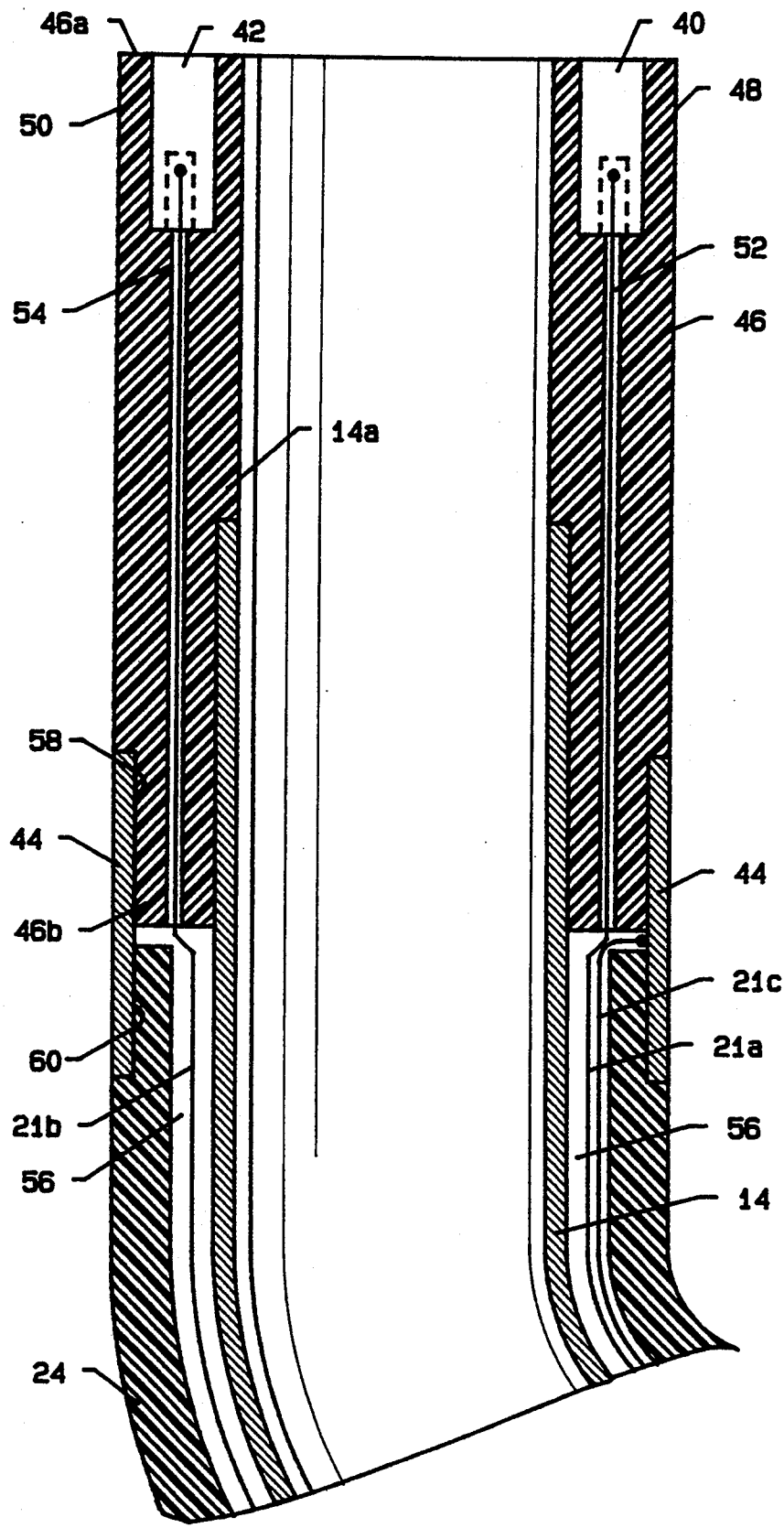
FIG. 4 illustrates a cross-sectional view of the electrode tip.

FIG. 4 illustrates a cross-sectional view of FIG. 3 where all numerals correspond to those elements previously described. The polymer member 46 aligns over and about the tip end 14a of the stainless steel support tube 14. Bipolar electrodes 40 and 42 are embedded in cylindrical cavities 48 and 50 in the distal end 46a of the polymer member 46. Longitudinal passageways 52 and 54 connect between the cylindrical cavities 48 and 50 and the proximal end 46b of the polymer member 46. An annular recess 58 at one end of the tubular polymer member 46 and another annular recess 60 at the end of the polymer sheath 24 accommodate the unipolar electrode 44. The stainless steel support tube 14 is of sufficient diameter to allow for an annular passageway 56 to be formed between the inner surface of the polymer sheath 24 and the outer surface of the stainless steel support tube 14. The wires 21a–21c connect the bipolar electrodes 40 and 42 and pass through the longitudinal passageways 52 and 54, respectively. The wire 21c connects to the unipolar electrode 44. The wires 21a–21c pass through the annular passageway 56 formed between the polymer sheath 24 and the stainless steel support tube 14 to the hand piece 16. The central lumen provides for the use of an interventional catheter, such as an ablation catheter 57, or any other diagnostic or interventional tool as may be deemed necessary.

MODE OF OPERATION

This mapping catheter is designed to treat tachyarrhythmia using a modified interoperative procedure and an energy source. It consists of two individual assemblies.

The first component is the mapping catheter. The mapping catheter is constructed of a plastic tube to which is affixed, at its distal end, a metal tip, which forms one pole of a mapping catheter. The ring could be subdivided, and the individual pieces are insulated with respect to each other so as to form a multiple pole system for purposes of mapping. The mapping catheter has a Y adapter at its proximal end to allow for insertion of an ablation catheter and flushing of the internal lumen.

The second component is an ablation catheter which can be part of the current mapping catheter or may be another catheter inserted into the mapping catheter. In the option where the mapping catheter itself is used, the electrode of the mapping catheter can be connected to a radio frequency generator or DC current module to ablate the arrhythmogenic sites. In the option of placing a second catheter down the lumen of the mapping catheter, other radio frequency (RF), direct current (DC) laser fibers of various configurations and cryroblation probes could be used to ablate the arrhythmogenic sites. In one embodiment, a laser ablation catheter which consists of a fiber optic cable, fixation wire, metal sensing tip, and internal flushing lumen. At the distal end, a metal tip housing the output end of the fiber, the fixed or movable fixation wire having single or multiple temperature sensing elements, and a water plenum created by the annular space of the metallic tip and the fiber cable. At the proximal end is a double Y-connector, which allows for a sensing of the tip electrical potentials, a flushing port for bathing the tip with sterile water during use, and an entry port for the fiber optic cable. The laser catheter assembly 57 is positioned inside the mapping catheter such that the tip of the laser catheter is even with or slightly ahead of that of the mapping catheter.

Both catheters contain markings to ascertain the relative position of each catheter with respect to each other, and to their position in the heart.

The apical catheter system is intended to treat tachyarrhythmia using a modified interoperative procedure. In this procedure, a thorocotomy is done and the patient is prepared for bypass surgery, which would be used only in the case of life threatening arrhythmia. Next, a small slit is made in the heart and a purse suture ring made. The hand-held probe is passed through the slit, and a suture ring is tightened around the myocardial tissue to seal the catheter against loss of blood. The mapping catheter is advanced through the hand-held probe until it comes in contact with the inside of the heart. The multiple tips of the mapping catheter are then used as a bipolar system to map the electrical potential in the area of contact. Alternatively, another catheter can be inserted into the mapping catheter and its tip can be used in conjunction with the mapping catheter to perform the bipolar sensing of electrical potentials.

In one application, a small slit is made in the apex of the left ventricle and the hand-held probe inserted through the slit. The hand-held probe is maneuvered inside the left ventricle and electrical potential and EKG signals are monitored until the probable site of the ventricular tachycardia is identified. At this point, a laser delivery catheter is inserted into the mapping catheter, and the fixation wire is extended into the myocardial tissue and flushing is commenced. Ventricular tachycardia is then induced and laser energy radiation of the myocardial tissue is initiated. The irradiation is continued until ventricular tachycardia has stopped. Attempts can be made to reinduce ventricular tachycardia to confirm that the site has been electrophysiologically altered, and that no secondary sites are present. If the ventricular tachycardia is not present, the procedure is completed by removing the catheter, suturing the hole in the left ventricle, and closing the chest wall. If ventricular tachycardia is still inducible, the above procedure is repeated.

The hand-held mapping catheter is suitable for sensing of the QRS and intercardiac potentials for subsequently ablating the active origin sites.

Various modifications can be made to the present invention without departing from the apparent scope hereof. The mapping catheter is also suitable for use with other energies such as DC, RF, or cryroblation. Any suitable energy which can be delivered through the electrodes can be utilized. The upper electrode can be divided into any number of separate insulated electrodes such as one to ten electrodes.

We claim:

1. A rigid mapping catheter for mapping of active origins of tachyarrhythmia, comprising:
    (a) handle means for providing a handhold, the handle means having a proximal end and a distal end and comprising a lumen and connectors for operatively coupling an external signal monitor which displays electrical potentials utilized in mapping active origins of tachyarrhythmia;
    (b) Y-connector means for providing multiple access ports to handle means, the Y-connector means comprising a lumen operatively connected to the handle means lumen at the handle means proximal end;
    (c) a rigid tubular member, having a proximal end and a distal end, which extends from the handle means distal end, the tubular member comprising annular passages operatively configured for retaining sensing electrodes, the rigid tubular member further comprising a lumen operatively configured to allow passage of medical apparati between the handle means lumen, the Y-connector means lumen, and the tubular member distal end when in contact with tissue to be sensed;
    (d) at least two sensing electrodes, coupled to the connectors for operatively coupling the external signal monitor, which are insulated with respect to each other and positioned on the tubular member distal end, the electrodes being operatively configured to facilitate direct contact with the tissue to be sensed; and,
    (e) a unipolar sensing electrode, coupled to another of the connectors for operatively coupling the external signal monitor, which is on the tubular member positioned, proximate to the tubular member distal end.

2. The mapping catheter of claim 1 further comprising means for connecting at least one of said sensing electrodes to an energy source for ablating at least one of the mapped active origins of tachyarrhythmia.

3. A catheter system, comprising:
    (a) a rigid mapping catheter for mapping of active origins of tachyarrhythmias, the mapping catheter comprising:
        (i) handle means for holding and positioning the mapping catheter, the handle means having a proximal end and a distal end and comprising a lumen and connectors for operatively coupling an external signal monitor which displays electrical potentials utilized in mapping active origins of tachyarrhythmia;
        (ii) Y-connector means for providing multiple access entries to the handle means, the Y-connector means comprising a lumen operatively connected to the handle means lumen at the handle means proximal end;
        (iii) a rigid tubular member, having a proximal end and a distal end, which extends from the handle means distal end, the tubular member comprising annular passages operatively configured for retaining sensing electrodes, the rigid tubular member further comprising a lumen operatively configured to allow passage of medical apparati between the handle means lumen, the Y-connector means lumen, and the tubular member distal end when in contact with tissue to be sensed;

(iv) at least two sensing electrodes, coupled to the connectors for operatively coupling the external signal monitor, which are insulated with respect to each other and positioned on the tubular member distal end, the electrodes being operatively configured to facilitate direct contact with the tissue to be sensed; and (v) a unipolar sensing electrode coupled to another of the connectors for operatively coupling the external signal monitor, which is spaced at a distance from the tubular member distal end; and (b) ablation means, operatively configured for passing through a central lumen of the rigid mapping catheter defined by the handle means lumen, Y-connector means lumen, and the tubular member lumen, for ablating a tachyarrhythmia site.

4. The catheter system of claim 3 wherein the ablation means comprises a laser catheter.

5. A method for sensing cardiac signals and for mapping active origins in a heart during surgical access, comprising the steps of:

(a) opening a thorax to expose the heart;
(b) cutting a small slit in the heart;
(c) inserting a rigid mapping catheter through the small slit into an inside chamber of the heart;
(d) positioning spaced distal insulated dipolar sensing electrodes to sense an electrogram in endocardial area of the heart in contact with the rigid mapping catheter, using the electrogram in mapping active origins; and
(e) positioning a unipolar sensing electrode spaced from said bipolar electrodes and referenced to sense an electrocardiogram (EKG) signal, using the EKG signal mapping active origins.

6. The method of claim 5, wherein the steps of positioning spaced distal insulated bipolar sensing electrodes and positioning a unipolar sensing electrode comprise positioning the bipolar and unipolar sensing electrodes to map arrhythmias.

7. The method of claim 6 wherein the steps of positioning spaced distal insulated bipolar sensing electrodes and positioning a unipolar sensing electrode comprise positioning the bipolar and unipolar sensing electrodes to map a particular type of arrhythmias known as ventricular tachycardias.

8. The method of claim 5 further comprising the step of passing energy through one of the sensing electrodes for ablating an active origin.

9. The method of claim 5 further comprising the step of passing a laser catheter through a lumen in said mapping catheter using the laser catheter for ablation of heart tissue.

* * * * *

UNITED STATES PATENT AND TRADEMARK OFFICE
CERTIFICATE OF CORRECTION

PATENT NO. : 5,409,008
DATED : April 25, 1995
INVENTOR(S) : Robert H. Svenson, et al.

It is certified that error appears in the above-indentified patent and that said Letters Patent is hereby corrected as shown below:

Col. 6, line 35, delete the comma after the word "monitor";
Col. 6, line 42, delete the comma after the word "monitor";
Col. 6, lines 43-44, delete the phrase "on the tubular member" and reinsert it after the word "positioned";
Col. 6, line 44, delete the comma after the word "positioned";
Col. 7, line 9, delete the comma after the word "monitor";
Col. 7, line 14, insert a comma after the word "electrode";
Col. 7, line 15, delete the comma after the word "monitor";
Col. 8, line 3, change "dipolar" to --bipolar--;
Col. 8, line 11, insert the word --in-- after the word "signal"; and
Col. 8, line 12, delete the commas after the number "5".

Signed and Sealed this

Second Day of April, 1996

*Attest:*

BRUCE LEHMAN

*Attesting Officer*  Commissioner of Patents and Trademarks